United States Patent [19]

Francis

[11] 4,091,103
[45] May 23, 1978

[54] QUINOLYL OR ISOQUINOLYL-LOWER-ALKOXY-PHENYLENE-AMINO DERIVATIVES

[75] Inventor: John E. Francis, Briarcliff Manor, N.Y.

[73] Assignee: Ciba-Geigy Corporation, Ardsley, N.Y.

[21] Appl. No.: 699,017

[22] Filed: Jun. 23, 1976

[51] Int. Cl.$^2$ .................. A61K 31/47; C07D 215/14; C07D 217/16
[52] U.S. Cl. .................. 424/258; 260/295 S; 260/296 AE; 260/288 CE; 260/288 D; 260/326.15; 260/326.5 R
[58] Field of Search ....... 260/296 AE, 288 R, 286 D, 260/288 CE; 424/258

[56] References Cited

PUBLICATIONS

Chemical Abstracts, vol. 67, abst. no. 82107k (1967), (abst. of German Pat. 1,231,704).
Chemical Abstracts, vol. 71, abst. no. 11825v (1969), (abst. of U.S. Pat. 3,462,446).
Chemical Abstracts, vol. 73, abst. no. 120509b (1970), (abst. of British Pat. 1,203,149).
Chemical Abstracts, vol. 80, abst, no. 14854v (1974), (abst. of Ger. Offen. 2,316,881).

*Primary Examiner*—Alan L. Rotman
*Attorney, Agent, or Firm*—Theodore O. Groeger

[57] ABSTRACT

New 1-(azacyclic aralkoxyphenyl)-2- or 3-(diphenylalkylamino)-alkanes, e.g those of the formula:

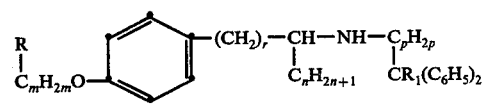

R = 5- or 6-membered, mono- or bicyclic, nitrogen-containing aromatic radical
m,n,p = 1-4; $r$ = 1 or 2;
$R_1$ = H or OH or therapeutically acceptable salts thereof are hypotensive and cardioactive agents.

5 Claims, No Drawings

QUINOLYL OR ISOQUINOLYL-LOWER-ALKOXY-PHENYLENE-AMINO DERIVATIVES

SUMMARY OF THE INVENTION

The present invention concerns and has for its object the provision of new 1-(azacyclic aralkoxyphenyl)-2 or 3-(bisarylalkylamino)-alkanes, more particularly of those corresponding to Formula I

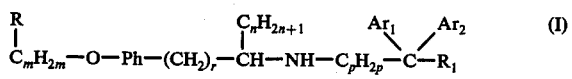

wherein R is an unsubstituted 5- or 6-membered mono- or bicyclic nitrogen-containing aromatic radical or such radical substituted by one or more than one member of lower alkyl, hydroxy, lower alkoxy, halogeno, trifluoromethyl or amino; Ph is unsubstituted phenylene, or phenylene substituted by one member listed for R, each of $Ar_1$ and $Ar_2$ is unsubstituted phenyl or phenyl substituted by one member listed for R, each of $m$, $n$ and $p$ is an integer from 1 to 4, $r$ is the integer 1 or 2 and $R_1$ is hydrogen or hydroxy, or of therapeutically useful salts thereof, as well as of corresponding pharmaceutical compositions and of methods for the preparation and application of said products, which are useful hypotensive and cardioactive agents.

DESCRIPTION OF THE PREFERRED EMBODIMENTS

Said azacyclic radicals contain preferably one nitrogen atom and are advantageously monocyclic, such as 2- or 3-pyrrolyl, 2-,3- or 4-pyridyl; but may also have two aromatic rings, such as 2-,3- or 4-indolyl or -quinolyl, 1-,3- or 4-isoindolyl or -isoquinolyl. They are preferably unsubstituted, but may also be substituted, advantageously by one or two members of the group consisting of lower alkyl, e.g. methyl, ethyl, n- or i-propyl or -butyl; hydroxy; lower alkoxy, e.g. methoxy, ethoxy, n- or i-propoxy or -butoxy; halogeno, e.g. fluoro, chloro or bromo; trifluoromethyl; or amino. The term "lower", referred to above or hereinafter in connection with organic radicals or compounds respectively, defines such with up to 7, preferably up to 4, advantageously such with one or two carbon atoms.

The phenylene radical Ph and phenyl radicals $Ar_1$ and $Ar_2$ are preferably unsubstituted 1,4-phenylene, but also 1,2- or 1,3-phenylene, or phenyl respectively, but also phenyl or phenylene substituted by one member of lower alkyl, lower alkoxy, halogeno or trifluoromethyl, e.g. those listed for R. The substituent $R_1$ is preferably hydrogen, but also hydroxy.

The lower alkyl group $C_nH_{2n+1}$ preferably represents methyl, but also any other member mentioned above. The lower alkylene group $C_mH_{2m}$ preferably stands for $(CH_2)_m$, especially methylene, but also for 1,1- or 1,2-ethylene, 1,1-, 2,2-, 1,2- or 1,3-propylene or -butylene; and $C_pH_{2p}$ preferably represents $(CH_2)_p$, especially 1,2-ethylene, but also any other of said alkylene groups.

Salts of the compounds of Formula I are preferably therapeutically acceptable acid addition salts, e.g. those derived from the acids listed below.

The compounds of the invention exhibit valuable pharmacological properties, primarily hypotensive, antihypertensive and bradycardic activity. This is demonstrable in animal tests, using advantageously mammals, e.g. rats, cats, dogs or monkeys, as test objects. The animals may either be normotensive or hypertensive, e.g. genetically or adrenal regeneration hypertensive rats. Said compounds can be applied to them enterally or parenterally, advantageously orally, or subcutaneously, intraveneously, intraperitoneally or intraduodenally, for example within gelatin capsules or in the form of starchy suspensions or aqueous solutions respectively. The applied dosage may range between about 0.1 and 100 mg/kg/day, preferably between about 1 and 50 mg/kg/day, advantageously between about 5 and 25 mg/kg/day. The lowering effect on the blood pressure is recorded either directly by means of a catheter, for example placed in the dog's femoral or the rat's caudal artery, or indirectly by sphygmomanometry at the rat's tail, and a transducer, expressing the blood pressure prior and after dosing in mm Hg. Thus, for example, the d,ρ-1-[4-(2-pyridylmethoxy)-phenyl]-2-(3,3-diphenyl-propylamino)-propane, a representative member of the compounds of the invention, advantageously in the form of its maleate, fumarate or oxalate, or preferably as the levorotatory antipode thereof, are very effective in said hypertensive rats at p.o. doses as low or lower than 5 mg/kg/day and maximally about 24 hours after dosing. Antihypertensive doses cause only minor impairment of sympathetic nerve function, unlike antihypertensive agents which act by adrenergic neuron blockade, as assessed by pressor responses to electrical stimulation of the spinal cord of pithed rats. Said member also differs from certain centrally acting antihypertensive agents which cause sedation. Furthermore, they do not produce sedation in monkeys at hyoptensive doses, as does α-methyldopa. Accordingly, the compounds of the invention are useful antihypertensive and bradycardic agents, for example in the treatment or management of primary or secondary hypertension, or angina pectoris respectively. They are also useful intermediates in the preparation of other valuable products, especially of pharmacologically active compositions.

Particularly useful for said purpose are compounds of Formula I, in which R is unsubstituted 2- or 3-pyrrolyl, 2-,3- or 4-pyridyl, 2-,3- or 4-indolyl or -quinolyl, 1-,3- or 4-isoindolyl or -isoquinolyl, or such radicals substituted by up to two members of lower alkyl, lower alkoxy or halogen, Ph is 1,3- or 1,4-phenylene, (lower alkyl)-1,3- or 1,4-phenylene, (lower alkoxy)1,3- or 1,4-phenylene, (halogeno)-1,3- or 1,4-phenylene or (tri-fluoromethyl)-1,3- or 1,4-phenylene, each of $Ar_1$ and $Ar_2$ is phenyl, (lower alkyl)-phenyl, (lower alkoxy)-phenyl, (halogeno)-phenyl or (trifluoromethyl)-phenyl, each of $m$, $n$ and $p$ is an integer from 1 to 4, $r$ is the integer 1 or 2 and $R_1$ is hydrogen or hydroxy, or a therapeutically useful acid addition salt thereof.

Outstanding compounds of the invention due to their high degree of activity are those of Formula II

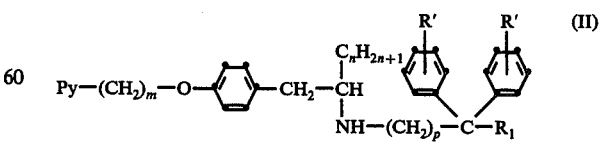

wherein Py is 2-, 3- or 4-pyridyl unsubstituted or substituted by one or two members of alkyl, alkoxy, fluoro or chloro, R' is hydrogen, alkyl, alkoxy, fluoro, chloro or trifluoromethyl, wherein alkyl or alkoxy has 1–4 carbon atoms, each of $m$, $n$ and $p$ is the integer 1 or 2, and $R_1$ is hydrogen or hydroxy, or therapeutically useful acid addition salts thereof.

Preferred are those compounds of Formula II, wherein Py is 2-, 3- or 4-pyridyl unsubstituted or substituted by one member of methyl, methoxy or chloro, R' is hydrogen, methyl, methoxy, fluoro, chloro or trifluoromethyl, each of $m$, $n$ and $p$ is the integer 1 or 2, and $R_1$ is hydrogen or hydroxy, or therapeutically useful acid addition salts thereof.

More preferred are those compounds of Formula II, wherein Py is 2- or 4-pyridyl, each of $m$ and $n$ is one, $p$ is two and each of $R_1$ and R' is hydrogen, or therapeutically useful acid addition salts thereof.

The compounds of the invention are prepared according to methods known per se, advantageously by:

(1) reducing carbonyl compounds of Formula III

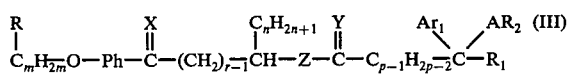
(III)

wherein one or both of X and Y is oxygen and the other is $H_2$ and Z is free or protected NH.

A protected amino group Z is preferably such, that can easily be liberated, e.g. by hydrolysis or hydrogenolysis, for example, an amide or advantageously benzylic grouping, such as a lower alkanoyl-, aralkanoyl- or α-aralkylamino group, e.g. $C_nH_{2n+1}$—CON or $Ar_1$—$C_nH_{2n}$—CON when Y = $H_2$, or $C_nH_{2n+1}$—CHAr$_1$—N when Y = O or $H_2$.

The reduction of the ketones and/or amides III is performed according to known methods, the former, for example, by the reaction of the Ketone with an arylsulphonylhydrazide followed by treatment with sodium borohydride. Amides are advantageously reduced with the use of reducing agents, such as simple or complex light metal hydrides, such as boranes or aluminum hydride, preferably alkali metal aluminum hydrides, e.g. lithium aluminum hydride, sodium aluminum hydride or lithium or sodium tri-lower alkoxy- or bis-alkoxyalkoxyaluminum hydrides, such as lithium tri-t. butoxy- or sodium bis-(2-methoxy-ethoxy)-aluminum hydride.

The starting material can be prepared according to methods known per se, e.g. those illustrated by the examples herein. Thus, for example, the products III are obtained from the corresponding phenolates, such as alkali metal, e.g. sodium or potassium salts, of the phenols HO—Ph—CX—$(CH_2)_{r-1}$—CH($C_nH_{2n+1}$)—Z—CY—$C_{p-1}H_{2p-2}$—CH($Ar_1$, $Ar_2$) and reactive esters of the alcohols R—$C_mH_{2m}$—OH, e.g. such derived from a strong inorganic or organic acid, preferably a hydrohalic, e.g. hydrochloric, -bromic or -iodic acid, or an alkane or benzene sulfonic acid, e.g. methane, p-toluene or m-bromobenzene sulfonic acid. Also amines R—$C_mH_{2m}$—O—Ph—CX—$(CH_2)_{r-1}$CH—$(C_nH_{2n+1})$—ZH can be reacted with reactive, functional derivatives of the acids HOOC—$C_{p-1}H_{2p-2}$C—$R_1(Ar_1Ar_2)$, e.g. halides or anhydrides thereof. The former phenols are either known or can be obtained by condensing compounds disclosed in Belgian Pat. No. 660,217, e.g. those of formula HO—Ph—CO—CHNH$_2$—$C_nH_{2n+1}$, with said alcohol or acid derivatives respectively, in subsequent steps and also according to the conditions mentioned under item 3) below.

Another method for preparing the compounds of Formula I consists in:

(2) reducing olefines or Schiff's bases of Formula IV

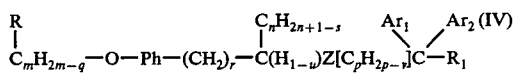
(IV)

wherein one of $q$, $s$ and $v$ is the integer 2 and the others 0 or 2, $u$ is 0, and Z is free or protected NH or Z is N, either $u$ is 1 or $v$ is 1 or 3 and the other integers have the meaning given above.

For materials in which $R_1$ is hydrogen, the desired compounds are prepared by reducing olefins or Schiff's bases of Formula IVa

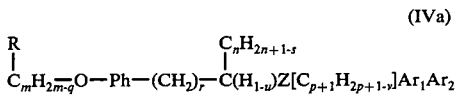
(IVa)

wherein one of $q$, $s$ and $v$ is the integer 2 and the others 0 or 2, $u$ is 0 and Z is free or protected NH, or Z is N, either $u$ is 1 or $v$ is 1 or 3 and the other integers have the meaning given above.

The reduction of compounds IV and IVa is carried out according to known methods, for example with the use of hydrogen in the presence of catalysts, e.g. platinum or nickel catalysts, or with nascent hydrogen, e.g. generated electrolytically, which is advantageously applied to the Schiff's bases IV and IVa. They can also be reduced with the reducing agents mentioned under item 1, preferably with simple light metal hydrides, e.g. boranes. Schiff's bases with $n=0$, $u$ or $v=1$(or 3) respectively, can also be reduced with $C_nH_{2n+1}$-Grignard compounds, e.g. lower alkyl-magnesium halides, and the metal adducts hydrolysed with water or aqueous ammonium salts, in order to obtain compounds of Formula I with $n=1$ to 4 or branched $C_pH_{2p}$.

The olefines IV and IVa are obtained analogous to the carbonyl compounds III, by choosing the above condensations with the corresponding unsaturated compounds, i.e. reactive esters of the alcohol R—$C_mH_m$—$_q$—OH, or derivatives of the acid HOOC[$C_{p-1}H_{2p-2-v}$]CR$_1$Ar$_1$Ar$_2$ for preparing IV or derivatives of the acid HOOC[$C_pH_{2p-1-v}$]Ar$_1$Ar$_2$ for preparing IVa and reducing in any resulting amide the carbonyl group with said reducing agents mentioned under item 1), preferably with complex light metal hydrides, e.g. lithium aluminum hydride. The Schiff's bases IV are obtained from the corresponding free or protected amines HO—Ph—$(CH_2)_r$—CHNH$_2$—$C_nH_{2n+1-s}$ by condensation with the aldehyde OHC—$[C_{p-1}H_{2p-2-v}]$CR$_1$Ar$_1$Ar$_2$, followed by a reactive ester of R—$C_mH_{2m-q}$OH if necessary.

Schiff's bases IV are also obtained from the corresponding free or protected ketones HO—Ph—$(CH_2)$—$_r$—CO—$C_nH_{2n+1-s}$ by condensation with an amine H$_2$N[$C_pH_{2p-v}$]CR$_1$Ar$_1$Ar$_2$, followed by a reactive ester of R—$C_mH_{2m-q}$OH if necessary.

The Schiff's bases IVa are obtained from the free or protected amines HO—PH—$(CH_2)_r$—CHNH$_2$—$C_nH_{2n+1-s}$ by condensation with the aldehyde OHC—$[C_pH_{2p-1-v}]$Ar$_1$Ar$_2$, followed by a reactive ester of R—$C_mH_{2m-r}$—OH. Schiff's bases IVa are also obtained from the corresponding free or protected ketones HO—Ph—$(CH_2)_r$—CO—$C_nH_{2n+1-s}$ by condensation with an amine H$_2$N—$[C_{p+1}H_{2p+1-v}]$Ar$_1$Ar$_2$, followed by a reactive ester of R—$C_mH_{2m-q}$—OH if necessary.

Another method for preparing the compounds of Formula I consists in:

(3) condensing compounds of Formulae V and VI (V) $R-C_mH_{2m}-T$ + $U-C_pH_{2p}-CR_1AR_1AR_2$ (VI)

or reactive salts thereof, wherein one of T and U is the group $(O-Ph-(CH_2)_r-CH(C_nH_{2n+1})Z'')H$ in which $Z''$ is free or protected NH, and the other of T and U is reactively esterified OH, or U is amino and T said moiety wherein $Z''$ is reactively esterified OH, e.g. bromo.

The condensation of V and VI is preferably carried out with the use of reactive salts of the phenols or amines respectively, such as alkali metal, e.g. sodium or potassium salts, or in the presence of condensing agents, neutralizing the eliminated acids (TH, UH or $Z''H$) and/or attracting any water formed, such as inorganic or organic (nitrogen) bases, e.g. alkali or alkaline earth metal carbonates or hydrogencarbonates; tri-lower alkylamines or pyridines, or anhydrous forms of salt hydrates or azeotropic solvents respectively.

The compounds V and VI are similarly prepared as the above starting material, e.g. from $HO-Ph-(CH_2)_r-CH(C_nH_{2n+1})Z''$ by condensation with $R-C_mH_{2m}-T$ or $U-C_pH_{2p}-CH(Ar_1Ar_2)$, wherein T is reactively esterified OH and one of U and $Z''$ is T and the other $NH_2$. The protection of the amino groups can be carried out in the usual manner, e.g. similar to the procedures shown in French Pat. Nos. 2,013,686 and 2,013,689.

Either in the course of the above reactions 1 to 3, or subsequently, any protected or metallized amino group Z and $Z''$ can be liberated in the usual manner, e.g. by hydrolysis of the amide groupings, or by hydrogenolysis of the α-aralkyl groups, e.g. either with the use of water alone or preferably aqueous acids or bases respectively, advantageously aqueous mineral acids or alkali metal hydroxides or catalytically activated hydrogen.

The resulting compounds of the invention can be converted into each other according to known methods. Thus, for example, any resulting halogen compound can be dehalogenated either in the course of any of the above hydrogenations or subsequently under more drastic conditions, e.g. higher temperature and/or pressure, and the course of these reactions is easily observed and controlled by the amount of consumed hydrogen. Moreover, the compounds of the invention are obtained in the free form or in the form of their acid addition salts, depending on the conditions under which the process is carried out. Salts that are obtained can be converted into the free bases in known manner, for example, with ammonia, alkalies or ion exchangers. Free bases that are obtained can be converted into salts by neutralization with acids, especially those that are suitable for the formation of therapeutically useful acid addition salts. Such acids are inorganic or organic acids, for example, mineral acids, such as a hydrohalic, e.g. hydrochloric or hydrobromic acid; sulfuric, phosphoric, nitric or perchloric acid; aliphatic or aromatic carboxylic or sulfonic acids, such as formic, acetic, propionic, succinic, glycollic, lactic, malic, tartaric, citric, ascorbic, maleic, hydroxymaleic, pyruvic, phenylacetic, benzoic, aminobenzoic, anthranilic, 4-hydroxybenzoic, salicylic, 4-aminosalicylic, embonic, nicotinic, methanesulfonic, ethanesulfonic, hydroxyethanesulfonic, ethylenesulfonic, halobenzenesulfonic, toluenesulfonic, naphthalenesulfonic, sulfanilic or cyclohexylsulfamic acid; methionine, tryptophane, lysine or arginine. These or other salts, for example, the picrates, can also be used in the purification of the free compounds. In view of the close relationship between the salts and the free compounds, whenever such is referred to in this context, a corresponding salt is also intended, provided such is possible or appropriate under the circumstances.

Resulting mixtures of isomers can be separated into the single isomers by methods in themselves known, e.g. by fractional distillation, crystallization and/or chromatography. Racemic products can likewise be resolved into the optical antipodes, for example, by separation of diastereomeric salts thereof, e.g. by the fractional crystallization of d- or l-tartrates.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage of the process is used as starting material and any remaining steps are carried out, or the process is discontinued at any stage thereof, or in which the starting materials are formed under the reaction conditions, or in which the reaction components are used in the form of their salts or optically pure antipodes.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preserving, stabilizing wetting or emulsifying agents, solution promoters, salts for regulating the osmotic pressure and/or buffers. They may also contain other therapeutically valuable substances. Said pharmaceutical compositions are prepared according to conventional mixing, granulating or coating methods respectively and contain about 0.1 to 75% preferably about 1 to 50% of the active ingredient.

The following examples, illustrating the invention, are not to be construed as being limitations thereon. Temperatures are given in degrees Centigrade, all parts wherever given are parts by weight and, if not specified, all evaporations are carried out under reduced pressure, e.g. at 10–20 Torr.

EXAMPLE 1

The mixture of 10 g of 1-(4-hydroxyphenyl)-2-(3,3-diphenylpropylamino)-propane (prepared as described by Ehrhart et al, U.S. Pat. No. 3,152,173), 50 ml of dimethylsulfoxide, 5 ml of water and 2.4 g of sodium hydroxide is stirred at 60° for 1 hour. To this are added 4.9 g of 4-pyridylmethyl chloride hydrochloride and the whole is stirred under nitrogen at ambient temperature over night. The mixture is poured into 300 ml of water and extracted with methylene chloride. The extract is treated with charcoal, dried and evaporated. The residue is taken up in diethyl ether, the solution washed with 3N aqueous sodium hydroxide, dried and evaporated. The residue is dissolved in the minimum amount of methanol-ethyl acetate, the solution neutralized with methanolic fumaric acid and refrigerated, whereupon the d,p-1-[4-(4-pyridylmethoxy)-phenyl]-2-(3,3-diphenylpropylamino)-propane fumarate of the formula

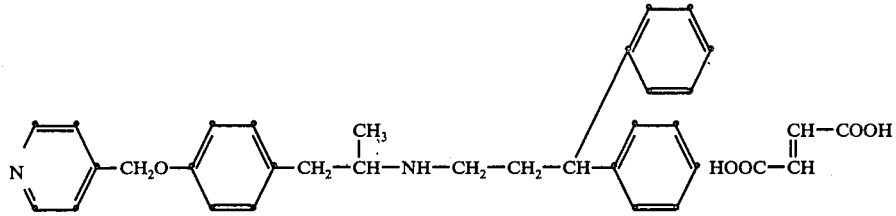

separates, melting at 142°–144°.

EXAMPLE 2

The mixture of 18.8 g of p-1-(4-hydroxyphenyl)-2-(3,3-diphenylpropylamino)-propane hydrochloride, 150 ml of dimethylsulfoxide and 15 ml of 10N aqueous sodium hydroxide is stirred for 75 minutes at room temperature under nitrogen, whereupon 8.2 g of 4-pyridylmethyl chloride hydrochloride are added and the whole is stirred 20 hours at room temperature. The mixture is poured into 1.5 lt of water, extracted with methylene chloride, the extract dried and evaporated. The residue is dissolved in 500 ml of diethyl ether, the solution washed with 2N aqueous sodium hydroxide and saturated aqueous sodium chloride, dried and evaporated. 20.6 g of the residue are dissolved in the minimum amount of isopropanol and the solution combined with that of 5.48 g of fumaric acid in isopropanol, the mixture diluted with ethyl acetate and filtered. The residue is taken up in 2N aqueous sodium hydroxide, the mixture extracted with ethyl acetate, the extract dried and evaporated. The residue is taken up in isopropanol and the solution neutralized with isopropanolic oxalic acid, to yield the p-1-[4-(4-pyridylmethoxy)-phenyl]-2-(3,3-diphenylpropylamino)-propane hemioxalate melting at 199°–200°, $[M]_D = -35.4°$ (5% in methanol). Analogously the acetate hemihydrate is prepared, m.p. 85°–88°, $[M]_D = -48.2°$ (c = 1 in methanol) and the diacetone-2-keto-L-gulonate, m.p. 211°–212°, $[M]_D = -89.6°$ (c = 0.5 in dimethylacetamide).

The starting material is prepared as follows: The mixture of 23 g of p-1-(4-hydroxyphenyl)-2-aminopropane, 31.2 g of 3,3-diphenylacrolein, 150 ml of anhydrous ethanol and 4 g of 10% palladium on charcoal is hydrogenated at 3.3 atm. for 6 hours. It is filtered, the filtrate evaporated, the residue dissolved in 400 ml of isopropanol and the solution combined with 12.5 ml of concentrated hydrochloric acid. After standing overnight the precipitate is collected and washed with isopropanol and diethyl ether, to yield the p-1-(4-hydroxyphenyl)-2-(3,3-diphenylpropylamino)-propane hydrochloride melting at 244°–247°; $[M]_D = -35.1°$ (5% in methanol).

EXAMPLE 3

The mixture of 5.7 g of 1-(4-hydroxyphenyl)-2-(3,3-diphenylpropylamino)-propane hydrobromide, 3.2 g of said propane hydrochoride, 50 ml of dimethylsulfoxide and 6.7 ml of 10N-aqueous sodium hydroxide is stirred at 60° for 1 hour. It is cooled with ice, combined with 3.6 g of 3-pyridylmethyl chloride hydrochloride, the mixture stirred until all solids are dissolved, heated to 60° for 1 hour and stirred for 18 hours at room temperature. It is poured into ice-water, extracted with ethyl acetate, the extract washed with saturated aqueous sodium chloride dried and evaporated. The residue is taken up in ethanol, the solution acidified with 2.45 g of maleic acid in ethanol, and diluted with diethyl ether, to yield the d,p-1-[4-(3-pyridylmethoxy)-phenyl]-2-(3,3-diphenylpropylamino)-propane maleate melting at 135°–137°.

EXAMPLE 4

To the solution of 10.36 g of d,p-1-(4-hydroxyphenyl)-2-(3,3-diphenylpropylamino)-propane in 75 ml of dimethylsulfoxide and 6 ml of 10N aqueous sodium hydroxide, stirred for 45 minutes under nitrogen, 4.92 g of 2-pyridylmethyl chloride hydrochloride in 50 ml of dimethylsulfoxide are added dropwise and the mixture is stirred for 18 hours of room temperature. It is poured into 500 ml of water, extracted with methylene chloride, the extract dried and evaporated. The residue is dissolved in the minimum amount of ethanol and the solution neutralized with ethanolic diacetone-2-keto-L-gulonic acid hydrate and the mixture diluted with water to incipient turbidity. The precipitate formed on cooling is collected and recrystallized from aqueous ethanol, to yield the d,p-1-[4-(2-pyridylmethoxy)-phenyl]-2-(3,3-diphenyl-propylamino)-propane diacetone-2-keto-L-gulonate of the formula

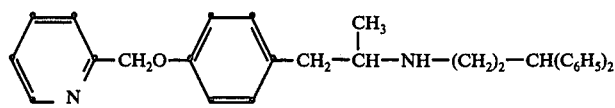

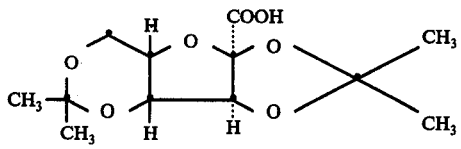

melting at 147°–150°, $[M]_D = -48.3°$ ($c = 1$ in methanol).

Analogously its levorotatory isomer is obtained as hemidrate (from the starting material of Example 2), melting at 180°–182°, $[M]_D = -81.3°$, or the corresponding maleate melting at 164°–165°, $[M]_D = -52.5°$ (for both: c = 1 in methanol).

Reacting said d,p- starting material with an equivalent amount of α-quinolylmethyl chloride hydrochloride, the d,p-1-[4-(2-quinolylmethoxy)-phenyl]-2-(3,3-diphenylpropylamino)-propane is obtained, the maleate of which melts at 177°–179°.

EXAMPLE 5

Preparation of 10,000 tablets each containing 50.0 mg of the active ingredient:

| Formula: | |
|---|---|
| p-1-[4-(2-pyridylmethoxy)-phenyl]-2-(3,3-diphenylpropylamino)-propane maleate | 500.00 g |
| Lactose | 1,706.00 g |
| Corn starch | 90.00 g |
| Polyethylene glycol 6,000 | 90.00 g |
| Talcum powder | 90.00 g |
| Magnesium stearate | 24.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene glycol in 180 ml of water. The paste formed is added to the powders which are granulated, if necessary, with an additional amount of water. The granulate is dried overnight at 35°, broken on a screen with 1.2 mm openings and compressed into tablets using concave punches with 7.1 mm diameter, uppers bisected.

Preparation of 10,000 capsules each containing 100 mg of the active ingredient:

| Formula: | |
|---|---|
| d,p-1-[4-(4-pyridylmethoxy)-phenyl]-2-(3,3-diphenylpropylamino)-propane fumarate | 1,000.0 g |
| Lactose | 2,800.0 g |
| Talcum powder | 200.0 g |

Procedure:

All the powders are passed through a screen with openings of 0.6 mm. Then the drug substance is placed in a suitable mixer and mixed first with the talcum, then with the lactose until homogenous. No. 1 capsules are filled with 400 mg each, using a filling machine.

Analogously tablets and capsules are prepared from the remaining compound illustrated by the previous examples.

I claim:

1. A compound of the formula

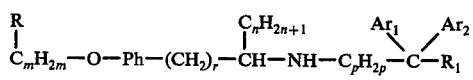

wherein R is unsubstituted 2-, 3- or 4-quinolyl, 1-,3- or 4-isoquinolyl, or such radicals substituted by one or two members selected from lower alkyl, hydroxy, lower alkoxy, halogeno, trifluoromethyl and amino; Ph is unsubstituted phenylene, or phenylene substituted by one member listed for R, each of $Ar_1$ and $Ar_2$ is unsubstituted phenyl or phenyl substituted by one member listed for R, each of m, n and p is an integer from 1 to 4, r is the integer 1 or 2 and $R_1$ is hydrogen or hydroxy, or a therapeutically useful acid addition salt thereof.

2. A compound as claimed in claim 1, in which formula R is unsubstituted 2-,3- or 4-quinolyl or 1-,3- or 4-isoquinolyl or such radicals substituted by up to two members of lower alkyl, lower alkoxy or halogen, Ph is 1,3- or 1,4-phenylene, (lower alkyl)-1,3- or 1,4-phenylene, (lower alkoxy)-1,3- or 1,4-phenylene, (halogeno)-1,3- or 1,4-phenylene or (trifluoromethyl)-1,3- or 1,4-phenylene, each of $Ar_1$ and $Ar_2$ is phenyl, (lower alkyl)-phenyl, (lower alkoxy)-phenyl, (halogeno)-phenyl or (trifluoromethyl)-phenyl, each of m, n and p is an integer from 1 to 4, r is the integer of 1 or 2 and $R_1$ is hydrogen or hydroxy, or a therapeutically useful acid addition salt thereof.

3. A compound as claimed in claim 1 and being the d,p-1-[4-(2-quinolylmethoxy)-phenyl]-2-(3,3-diphenylpropylamino)propane.

4. A compound as claimed in claim 1 and being the levorotatory optical antipode thereof.

5. A hypotensive pharmaceutical composition comprising an antihypertensively effective amount of a compound as claimed in claim 1, together with a pharmaceutical excipient suitable for enteral or parenteral application.

* * * * *